United States Patent [19]

Clement

[11] Patent Number: 5,786,383

[45] Date of Patent: Jul. 28, 1998

[54] PHARMACEUTICAL PREPARATION

[76] Inventor: Bernd Clement, Johann-Fleck-Strasse 27, D-24106 Kiel, Germany

[21] Appl. No.: 571,848

[22] PCT Filed: Jun. 28, 1994

[86] PCT No.: PCT/DE94/00756

§ 371 Date: Feb. 6, 1996

§ 102(e) Date: Feb. 6, 1996

[87] PCT Pub. No.: WO95/01168

PCT Pub. Date: Jan. 12, 1995

[30] Foreign Application Priority Data

Jun. 28, 1993 [DE] Germany ............ 43 21 444.4

[51] Int. Cl.[6] .......... A61K 31/15; C07C 251/36
[52] U.S. Cl. .......... 514/633; 564/229; 564/225; 514/364; 514/631
[58] Field of Search .......... 548/131; 564/229; 514/633, 256, 361

[56] References Cited

U.S. PATENT DOCUMENTS

| | | | |
|---|---|---|---|
| 3,658,832 | 4/1972 | Asato et al. | 260/307 F |
| 3,795,735 | 3/1974 | Asato et al. | 424/248 |
| 3,819,702 | 6/1974 | Lafon et al. | 260/564 G |
| 4,921,852 | 5/1990 | Murata et al. | 514/210 |
| 5,026,724 | 6/1991 | Logan et al. | 514/443 |
| 5,138,064 | 8/1992 | Murata et al. | 548/127 |
| 5,322,858 | 6/1994 | Canfield et al. | 514/635 |

FOREIGN PATENT DOCUMENTS 24 26 878  1/1976  Germany .

OTHER PUBLICATIONS

Archiv Der Pharmazie, vol. 325, No. 1, 1992, pp. 61–62.
Arzneimittel Forschung, vol.. 35, No. 7, 1985, pp. 1009–1014.
Arzeimittel Forschung, vol. 42, No. 12, 1992, pp. 1497–1504.
Indian Journal of Chemistry, vol. 22B, No. 9, 1983, pp. 898–900.
Journal of Medicinal Chemistry, vol. 12, No. 3, 1969, pp. 381–383.
Journal of Medicinal Chemistry, vol. 18, No. 4, 1975, pp. 430–432.
The Merck Index, 1989, Merck & Co., Inc. Eleventh Edition, p. 515, paragraph 3256, p. 815, paragraph 5067, p. 1128, paragraph 7071.

*Primary Examiner*—Alan L. Rotman
*Assistant Examiner*—Charanjit S. Aulakh
*Attorney, Agent, or Firm*—Barnes & Thornburg

[57] ABSTRACT

The invention relates to a novel pharmaceutical preparation, containing an active ingredient of at least one active amidine group, which contains a pharmaceutically active amidine group which may be a administered orally.

The amidine group is present in the form of a compound selected from the group:

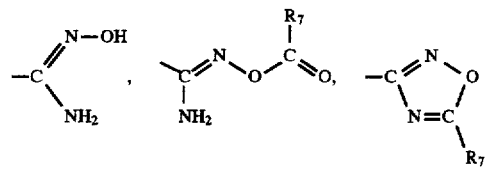

wherein $R_7$ is hydrogen, an alkly residue and/or an aryl residue.

24 Claims, No Drawings

PHARMACEUTICAL PREPARATION

This application is a 371 of PCT/DE94/00756 which is now published as WO 95/01168 on Jan. 12, 1995.

The present invention relates to a novel pharmaceutical preparation, containing an active ingredient having at least one active amidine group, and to its use.

In order to treat pneumocystis carinii pneumonia, which affects almost 70% of all AIDS patients without prophylactic measures in the course of their illness, it is known to use aqueous solutions of pentamidine diisethionate with the aid of special atomisers in aerosol form. In this case this known pentamidine diisethionate has a structure as illustrated by the following formula P:

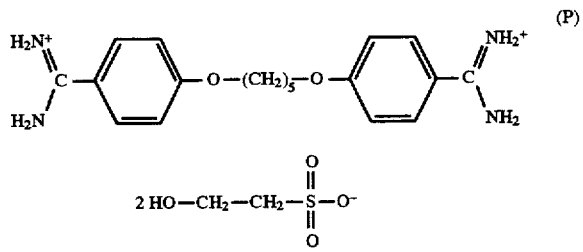

However, the known pentamidine isethionate has the disadvantage that when applied orally it is poorly resorbed, and thus with this type of administration cannot exert any pharmacological effect in the body. For this reason the preparation has been given to the patients intramuscularly or intravenously. The galenic formulations available for this, however, have serious side-effects, which are to be ascribed to the form of administration.

In intravenous administration, intense blood-pressure drop (hypotonia) linked with malaise and vomiting, to the extent of unconsciousness, can occur. Nor does intramuscular administration offer any particular advantages, as frequently extreme pain at the point of injection, leading to tissue necrosis, which require tedious follow-up treatment, are observed.

These side-effects do not occur with the atomisation of pentamidine diisethionate already described. However, only slight to mildly serious cases of pneumocystis carinii pneumonia may be treated by atomisation, as a severe attack renders inhalation of the aerosol impossible, or at least extremely difficult. This form of administration also requires a high degree of cooperation from the patient, as he must learn the correct inhalation technique in order to achieve a uniform distribution of the active ingredient, which is essential for successful therapy.

Some serious disadvantages, however, stand in the way of this form of administration, with its low systemic stress and ensuing lower toxicity. Each administration requires an ambulatory stay in hospital, during which at least one doctor should be present as, in aerosol therapy, frequently (in up to 15% of administrations), bronchial spasm can occur, necessitating medical countermeasures. Also, pulmonary administration requires a special atomiser which can generate a uniform particle size of 0.5 to 30 µm in diameter.

Depending on the type of atomiser and on the type of setting for this apparatus, sufficient concentrations of active ingredient frequently do not reach the required locus of action.

Cases with extrapulmonary involvement cannot be treated in this way. Connected with this, the recurrence rate of pneumocystis carinii pneumonia is increased when proper, regular prophylactic aerosol therapy is not carried out.

As stated above, pharmaceutical preparations containing pentamidine applied orally have practically no pharmacological effect. An essential condition for a therapeutic effect of an active ingredient given orally is its take-up from the gastro-intestinal tract. The most important mechanism for such membrane penetration in this case is passive diffusion. The degree of resorption by way of passive diffusion is dependent on lipophily, and is thus closely connected with the acidity or the basicity of the active ingredient. An intensely basic compound such as pentamidine ($pK_4=11.4$) is present in the stomach (pH=1) and in the gut (pH=7.4) in an almost totally ionised form. The molecule is hydrophilic during the entire gastro-intestinal passage. Oral resorption, which is connected with passage through a lipophilic membrane, therefore succeeds only to a very restricted degree. The high basicity of pentamidine is to be ascribed to its functional groups, i.e. the amidines. This is clearly the obstacle which explains why in the past oral administration resulted in entirely insufficient resorption and thus over a long period a very restricted pharmacological effect.

It is presumed that clearly all active ingredients having an amidine as a functional group reveal insufficient resorption when given orally.

Proceeding from this, the object of the present invention is to propose a pharmaceutical preparation containing a pharmaceutically effective amidine group which may be used orally.

This object is achieved by a pharmaceutical preparation with the characterising features of Patent claim 1. The sub-claims indicate advantageous further developments.

Accordingly, it is proposed according to the invention that the pharmaceutical preparation uses the pharmaceutical active ingredient which contains at least one amidine effective functional group in the form of at least one compound of the following formulae:

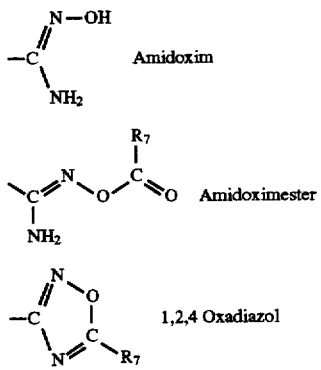

$R_7$ being an alkyl residue and/or an aryl residue. Amidoximes, amidoxime esters and 1, 2, 4 oxadiazoles are now orally resorbed, and converted back ("pro-drug" principle) by esterases and N reduction back into the actual active forms, the amidines. Thus there is available for oral administration an optimum medical form which may be used for the most varied indications. The pharmaceutical preparation proposed gains particular importance through the fact that the functional group amidines is an essential component of active ingredients, of varying degrees of importance, for various fields of appplication. Among others, the amidine group is a component of the following active ingredients or classes of ingredients: pentamidine, diminazen, isometamidium and thrombin inhibitors. Active ingredients containing an active amidine group can among other things be used for the following applications:

prophylaxis and therapy of visceral Leishmanioses and cutaneous Leishmanioses;

prophylaxis and therapy of trypanosomiasis (African sleeping sickness);

prophylaxis and therapy of pneumonia caused by pneumocystis carinii (PcP);

inhibition of proteases, thrombin inhibitors, fibrinogen receptor antagonists, platelet aggregation inhibitors;

inhibition of the growth of malign tumours (cancer chemotherapy);

lowering blood pressure;

N-methyl-D-aspartat receptor antagonists and thus neuroprotection.

The excellent resorptive capacity of the converted amidine functions in the gastro-intestinal tract is clearly due to the greatly reduced basicity and increased lipophily of the molecules of the active ingredient. As already stated, take-up from the gastro-intestinal tract is important for a therapeutic effect of an active ingredient after oral administration; this is closely connected with the acidity or basicity of the active ingredient. With chemical conversion of the amidine function as far as amidoxime esters or oxadiazol, however, basicity is reduced to a considerable degree. The $PK_2$ value of amidine, which stands at 11, drops when reaching amidoxime ester or oxadiazol to values beneath 5. The percentage proportion of free bases at pH 7.4 thus rises from amidine at zero to amidoxime ester or oxadiazol at 100. Thus in the gut, the main locus of resorption for active ingredients, amidoxime or amidoxime ester or oxadiazol, are present almost entirely in the form of free bases. In parallel with the reduction in basicity, due to the conversion of the amidine function undertaken, the lipophily of the corresponding active ingredients increases. The pharmaceutical preparations with converted amidine function proposed according to the invention thus show outstanding oral resorption capacity, and thus clearly increase the pharmacological effect of the amidine. The active ingredients proposed are not only resorbable in the stomach and/or gut, but are also capable of overcoming the blood/brain barrier. It is therefore sufficient if the active ingredient contains at least one active amidine group in the proposed form. The invention basically encompasses all active ingredients having at least one amidine group.

Accordingly, the active ingredient can contain a plurality of amidine groups (e.g. two with pentamidine); in that case at least one of these groups is modified in the way described above. In exactly the same way, mixtures of active ingredients may be used, insofar as at least on active ingredient has an amidine group.

Preferred active ingredients are chosen from: pentamidine, diminazen, isometamidium or thrombin inhibitors.

It is particularly preferred if the pharmaceutical preparation has an active ingredient such as that illustrated by the following general formula 1:

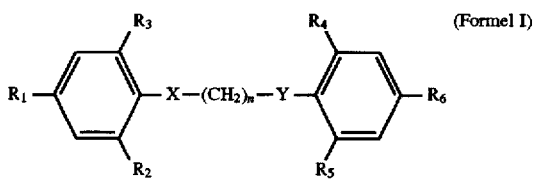

(Formel I)

In formula 1, $R_1$ and $R_6$ are identical or different, on condition however that $R_1$ and $R_6$ are not simultaneously an amidine group and means the groupings:

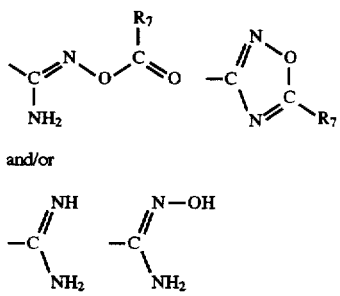

and/or

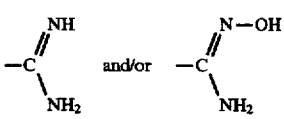

$R_7$ being hydrogen, an alkyl residue and/or an aryl residue, and its salts. Furthermore, in formula I $R_2$, $R_3$, $R_4$ and $R_5$ are identical or different and mean hydrogen, a $—NO_2$ group, halogens and/or an $OR_3$ grouping; $R_3$ in this case can be hydrogen and/or an alkyl group. X and Y, which may be identical or different, stand in formula I for oxygen, nitrogen or sulphur, while n is a whole number between 0 and 8.

It was discovered, surprisingly, that the pharmaceutical preparation according to the invention containing the active ingredient named above and shown in formula I has excellent prophylactic and therapeutic properties when the preparation according to the invention is used for prophylaxis and/or therapy of pneumocystis carinii pneumonia. In particular, it became apparent that the active ingredient shown in formula I does not possess the disadvantages already described in connection with the known pentamidine isethionate, and thus for example causing no tissue necrosis and hypotension when the pharmaceutical preparation according to the invention containing the active ingredient named above and shown in formula I is administered in a manner other than by atomisation. In addition, such an oral administration has the added advantage that the active ingredient contained in the pharmaceutical preparation according to the invention may be particularly simply and reproducibly dosed so that accordingly prophylaxis and/or therapy upon using the pharmaceutical preparation according to the invention is considerably improved. Salts of the active ingredient according to formula I also reveal a comparable effect.

In a further, particularly advantageous embodiment of the pharmaceutical preparation according to the invention, the preparation according to the invention has an active ingredient as shown above by the general formula I; in this embodiment, $R_1$ and $R_6$ are not simultaneously identical or different, and mean the groupings:

if n=5 and $R_2$ and $R_5$ are hydrogen, and if x and Y are identical, and mean oxygen.

Such an embodiment of the preparation according to the invention is particularly characterised in that, in comparison with pentamidine diisethionate, it has a greater lipophily and a lower basicity, and thus is orally resorbable and XNS-accessible, considerably improving the possibility of therapy and/or prophylaxis.

A further, likewise advantageous embodiment of the pharmaceutical preparation according to the invention has an active ingredient in which, in formula I, $R_1$ and $R_6$ are identical or different and mean the grouping:

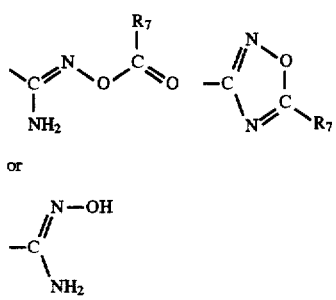

or

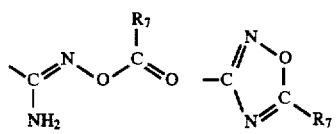

R7 being hydrogen, and alkyl residue and/or an aryl residue, and their salts.

Particularly when the active ingredient shown in formula I and contained in the pharmaceutical preparation according to the invention has a chemical structure in which $R_7$ means, in the general formulae:

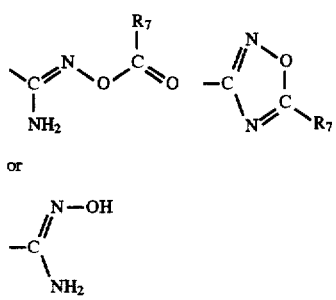

a $C_1$–$C_4$ alkyl group, particularly a methyl group, or a $C_{12}$–$C_{18}$ alkyl residue, the pharmaceutical effectiveness of such a preparation is yet further improved, so that accordingly the concentration of the active ingredient in the pharmaceutical preparation is reduced, or the daily dose to be administered can be reduced.

As already stated with respect to the preparation according to the invention, in the formula I $R_1$ and $R_6$ can be identical or different. Particularly when $R_1$ and $R_6$ are identical in formula I, an active ingredient built up in this way may be particularly easily synthesised, as in this way costly isolation of such an active ingredient may be eliminated by synthesis.

As already stated, in the general formula I n can mean a whole number between 0 and 8. Preferably, however, the preparation according to the invention has a structure in which n stands for a whole number between 2 and 6.

In another advantageous further development of the preparation according to the invention, characterised by an extremely high degree of pharmaceutical effectiveness and facility for simple synthesis of the active ingredient of the general formula I, $R_2$, $R_3$, $R_4$ and/or $R_5$ mean an $OCH_3$ group.

The concentration of the active ingredient in the pharmaceutical preparations according to the invention depends on the respective case of administration and on the daily dosage. The preparation according to the invention preferably has the active ingredient according to formula I in a concentration between 0.01% by weight and 50% by weight, particularly in a concentration between 1% by weight and 20% by weight.

In the above it has always been a matter, in connection with the pharmaceutical preparation according to the invention, of the preparation according to the invention containing the active ingredient. Naturally, however, it is also possible to provide here a mixture of active ingredients.

In the oral administration according to the invention it is now ensured to a particular degree that the active ingredient can be reproducibly dosed; this has a decisive influence on therapy and prophylaxis in the treatment of pneumocystis carinii pneumonia. Furthermore, oral administration ensures that even severe cases with extrapulmonary involvement, which may not be treated, or only with difficulty, by aerosol, can now be made accessible to therapy.

It also became apparent, surprisingly, that the pharmaceutical preparation according to the invention can be used not only for prophylaxis and/or therapy of pneumocystis carinii pneumonia, but also for prophylaxis and/or therapy of animal or human trypanosome infections and/or of Leishmanioses. Here also oral administration of the pharmaceutical preparation according to the invention is indicated; in this oral administration, surprisingly, the side-effects already described with respect to pentamidine isethionate do not occur.

This high degree of effectiveness of the pharmaceutical preparation according to the invention, as already described, is ascribed to the fact that the active ingredient in formula I, due to its lower basicity and higher lipophily compared to pentamidine diisethionate, is resorbed to a large extent when administered orally during its passage through the gastrointestinal tract. During or after completed resorption, metabolisation takes place in the body, to provide the corresponding diamidine or diamidine derivate which due to its hydrophily in oral administration would not be resorbed, or only slightly, in the gastro-intestinal tract, but otherwise has the desired pharmaceutical effectiveness.

The metabolisation briefly described above, and taking place in vivo, of the pharmaceutical preparation according to the invention, may be diagrammatically illustrated by the layout reproduced in the following, using the example of variants of embodiments of the pharmaceutical preparations according to the invention.

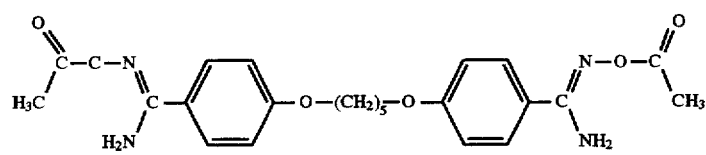

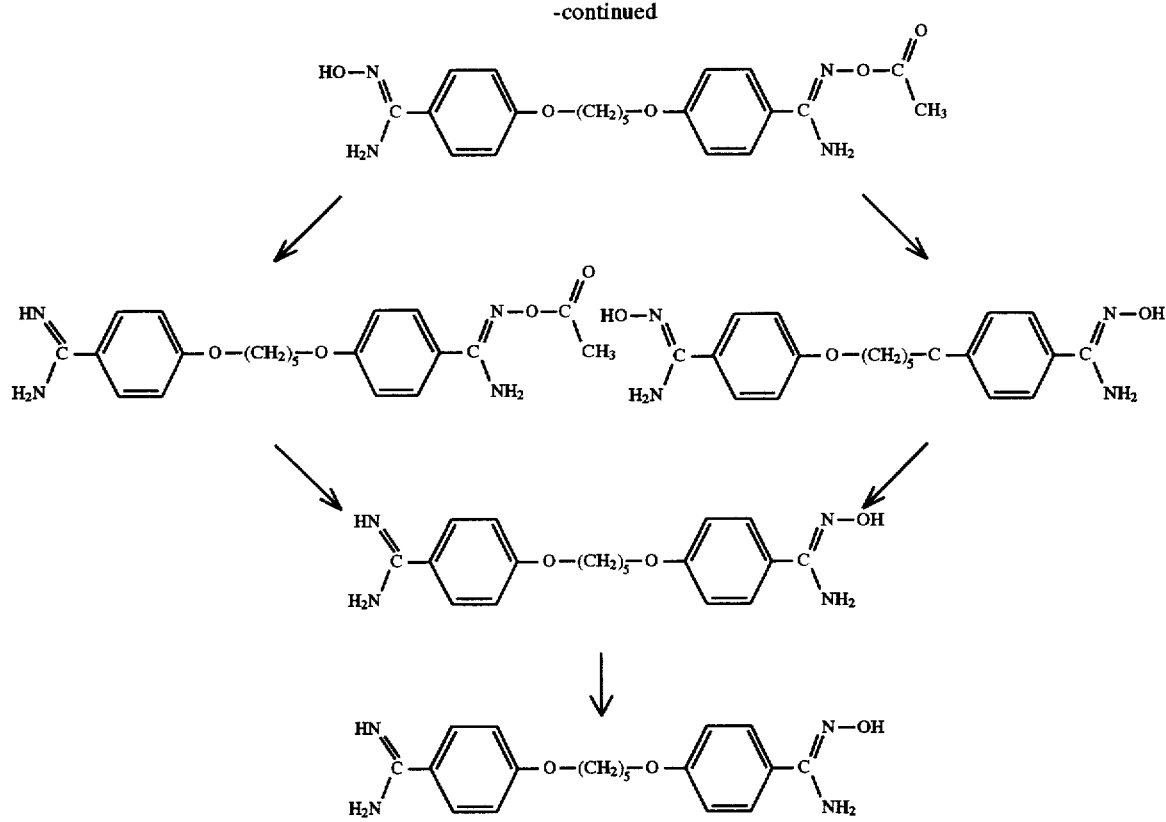

A particularly suitable embodiment of the pharmaceutical preparations according to the invention has an active ingredient as characterised by the formulae II, III or IV shown below:

Basically it should be noted with respect to the active ingredients contained in the preparation according to the invention, for example as shown by the general formulae I to IV, that the improved pharmaceutical effect of the claimed

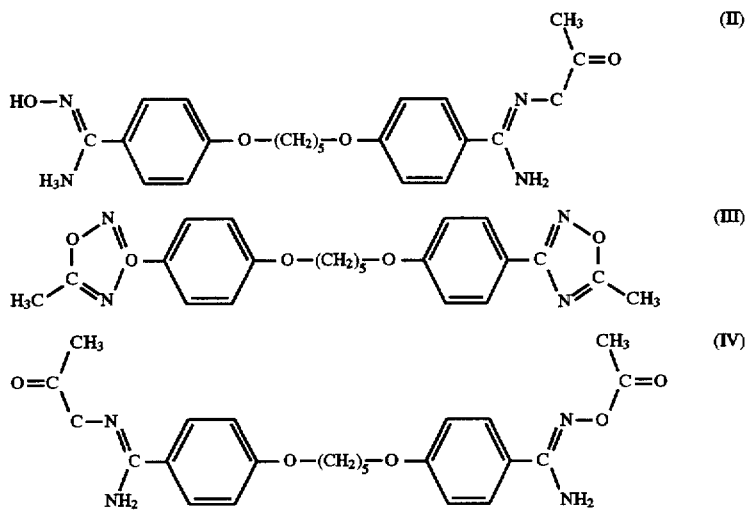

These special embodiments of the pharmaceutical preparations according to the invention, which contain the active ingredients according to the above formulae II to IV, may be used orally with outstanding success in the treatment and/or prophylaxis of pneumocystis carinii pneumonia and/or Leishmanioses, trypanosome infections and/or as cytostatics.

preparation according to the invention is ascribed among other things to the fact that the preparation according to the invention is clearly capable of overcoming the blood-brain barrier. This in turn means that with the pharmaceutical preparations according to the invention, particularly also in the embodiment described above and containing an active ingredient according to formulae II to IV, also successfully fight exciters which have attacked the patient's central nervous system; this is not possible with the known pentamidine diisethionate.

Thus the pharmaceutical preparation according to the invention makes available an effective agent for treatment of central nervous system forms of trypanosome infections, this agent not having the high toxicity of the arsenic-containing therapeutic means previously used for this purpose.

The form for oral administration may be prepared as a liquid, semisolid or solid preparation, particularly as tablets, sugar-coated pills, pellets or microcapsules. In this respect for embodiments in which liquid preparations are used, the active ingredient of mixture of active ingredients can be accommodated in a suitable non-toxic solvent such for example as water, univalent alcohols, particularly ethanols, multivalent alcohols, particularly glycerine and/or propandiol, polyglycols, particularly polyethylene glycols and/or miglycol, glycerine methylal, dimethylisosorbite, natural and/or synthetic oils and/or esters.

For the manufacture of semisolid or solid preparations, the conventional basic fillers may be used, such for example as bentonite, veegum, guar flour and/or cellulose derivatives, particularly methyl cellulose and/or carboxymethyl cellulose, as well as polymers from vinyl alcohols and/or vinyl pyrrodilones, alginates, pectins, polyacrylates, solid and/or liquid polyethyl glycols, paraffins, fatty alcohols, vaseline and/or waxes, fatty acids and/or fatty-acid esters. Also, fillers known per se may be contained in solid preparations, such for example as colloidal silicic acids, talcum, lactose, starch powder, sugar, gelatine, metallic oxides and/or metallic salts. Further possible additives are stabilisers, emulsifiers, dispersants and preservatives.

Advantageous further developments of the preparation according to the invention are indicated in the sub-claims.

The preparation according to the invention will be explained in more detail in the following with reference to embodiments given by way of example.

EMBODIMENT 1

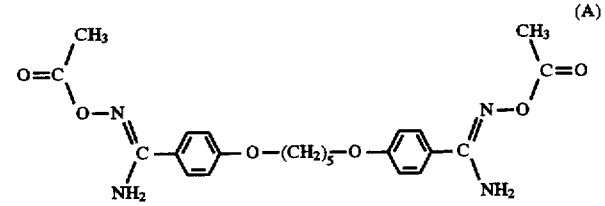

(A)

1 g of 4, 4'-pentamethylenedioxydibenzamidoxim was slowly mixed with approx. 10 ml freshly-distilled acetic anhydride, and left stirring for an hour at room temperature. At the end of the reaction the excess acetic anhydride was hydrolised with water. The resultant precipitate was fritted off and washed with 5 ml of 3n ammonia solution. The precipitate thus treated was washed with demineralised water until no further ammonia odour was discernible. Finally the precipitate was dried for one hour at 100° C. in a drying cabinet and recrystallised from acetonitrile.

| Yield: | 590 mg (48% of the theoretical yield), fine colourless needles |
|---|---|
| Melting: | 152° C. |
| IR Data KBr—: Compact in cm$^{-1}$: | 3500 (NH), 1752 (COOR), 1620 (C=N) |
| 1$_H$-NMR Data: | 1.61 1 (quint, 2H, —CH$_2$—); 1.81 |

-continued

| 400 MHZ spectrum: ([D$_6$]-DMSO) in ppm | (quint, 4H, 2-CH$_2$=); 2.15 (S, 6H, 2-CO—CH$_3$), 4.05(t, 4H, 2CH$_2$—O); 6.7(s, 4H, 2 HN$_2$); 7.34 (mc, AA' BB', 8H, aromatics-H) |
|---|---|
| $^{13}$C-NMR Data: 400 MHZ spectrum ([D$_6$]-DMSO) in ppm | 21.47(—CO—CH$_3$); 23.77(—CH$_2$); 29.94(—CH$_2$—); 69.13(—O—CH$_2$); 115.71(c-3 c-3'); 125.18 (—C=N—); 129.72(c-2, c02'); 157.69(C-4); 161.95(C-1); 170.15(—O—CO—CH$_3$) |
| C$_{23}$H$_{28}$O$_6$N$_4$(456.45) | Rep. C 60,52% H6, 18% N 12.27% Found. C 60, 58% H 6, 15% N 12.65% |

EMBODIMENT 2

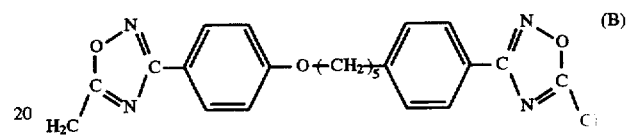

(B)

1 g of 4, 4'-pentamethylenedioxydibenzamidoxin were mixed with 10 ml freshly-distilled acetic anhydride and heated for 5 minutes with reflux. After cooling and hydrolysis of the excess acetic anhydride, a light yellow-coloured raw product was obtained, which was cleaned column-chromatographically (silica gel 60—CHCl$_3$/MeOH (V:V. 9:1), and was then recrystallised out of absolute ethanol.

| Yield: | 677 mg (60% of theoretical yield), fine, colourless needles. |
|---|---|
| Melting: | 137° C. |
| IR data (KBr—: compact in cm$^{-1}$ | 1620(C=N), 1275(C—O—C) |
| 1H-NMR data: 400 MHZ spectrum: (CDC13) in ppm | 1.69(quint, 2H, —CH$_2$—); 1.90 (quint, 4H, —CH$_2$—); 2.63(s, 6H, —CH$_3$), 4.06(t, 4H, —O—CH$_2$—), 7.48(mc, AA', BB', 8 aromatics H) |
| $^{13}$C-NMR data: 400 MHZ spectrum (CDCl$_3$) in ppm | 12.31(—CH$_3$); 22.65(—CH$_2$);28.37 (—CH$_2$); 67.78(—OCH$_2$—)114.69 C-3, C-3'); 119.11 (—C=N—); 128.88(C-2, C-2'); 161.30(C-4); 168.4(C-1); 176.18'(CH$_3$—C$^N$O) |
| C$_{23}$H$_{34}$O$_4$N$_4$ | Rep. C 65.70% H 5.75% N 13.32% Found. C 65.91% H 5.72% N 13.71% |

EMBODIMENT 3

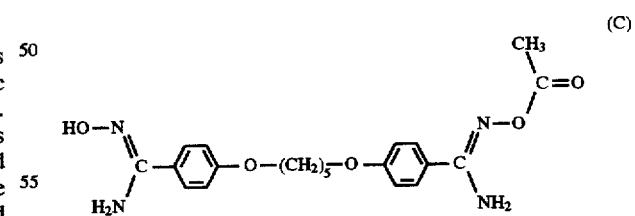

(C)

1 g of diacetyl-4, 4'-pentamethylenedioxydibenzamidoxim were dissolved in 100 ml of a solvent mix consisting of chloroform -methanol in a volume ratio of 9:1, and mixed with 5 g of pig pancreas lipase (PPL) (Company Sigmfa, type crude), and left stirring at room temperature. The reaction was pursued by thin-layer chromatography (silica gel—CHCl$_3$/eOH (9:1)) and interrupted as soon as pentamethylenedioxydibenzamidoxim had formed. Thereafter the lipase was filtered off and the clear filtrate saturated with oxalic acid, and mixed with a threefold volume of ether. The preparation was left to stand overnight in a refrigerator. The precipitated product was dissolved in chloroform/methanol (V;V 9:1) and cleaned by column chromatography (silica gel, chloroform/methanol (V;V 9:1)).

| Yield: | 40 mg (4.4% theoretical yield) |
|---|---|
| Melting: | 110° C. |
| IR data (KBr—: compact) in $cm^{-1}$ | 3510(NH), 3375(NH), 3200(OH), 1750 ($CH_3$—COOR), 1670(C=N—OH), 1620 (C=N—O—$COCH_3$) |
| $^1$H-NMR data: ([$D_6$]-DMSO) in ppm | 1.60(quint, 2H; $CH_2$), 1.82 (quint, 4 H, $CH_2$), 2.15(s, 3 H, —$COCH_3$); 4.06(t, 4 H, —O—$CH_2$); 6.65(s, 2 H, $NH_2$); 6.71(s, 2 H, $NH_2$); 7.32 (mc, AA'BB', 4 H, aromatics H), 7.34 (mc, AA'BB', 4 H, aromatics H); 10–12 (bs, 1 H, OH) |
| $^{13}$c-NMR data: ([$D_6$]-DMSO) in ppm | 19.90($CH_3$—); 22.18(—$CH_2$—); 28.23,(—$CH_2$—); 67.54(—O—$CH_2$—); 67.72(—O—$CH_2$); 114.13(C3', C3"); 114.32(C3, C3'), 122.31 (C=N—OH); 122.59(C=N—OCOR); 127.86(C2', C2"); 128.13(C2, C2'); 156.10(C4); 160(C4'); 160.51(C1); 162.57(C1'); 168.56 (O—$COCH_3$) |
| $C_{21}H_{26}O_5N_4$(414.45): | Rep. C 60, 85% H 6.27% N 13.51 Found. C 60.51% H 6.20% N 13.91% |

On the basis of the analytical data given above it can be ascertained that the products manufactured according to embodiments 1 to 3 have a chemical structure such as that shown above by the formulae A, B and C.

In order to prove their pharmaceutical effectiveness, the products described above were tested for their action against pneumocystis carinii.

For this purpose female Sprague-Dawley rats with an average weight of 200 to 220 g were given medicated drinking water containing 1.5 mg dexamethason and 10 mg ofloxazin per litre for a period of 8 weeks. At the end of this preliminary medication, a group of the animals were given bronchial lavage under nembutal narcosis to ascertain whether infection with pneumocystis carinii was present. The lavage material was centrifuged at 3,000 rpm, 10 µl of the resuspended product was dripped on to a specimen slide and allowed to dry in the air. The substances thus prepared were subjected to Giemsa rapid pigmentation and were microscopically examined. When an infection with pneumocystis carinii was detected, testing of the active ingredient could begin.

The animals were treated for 10 days with the active ingredients to be tested. At the end of this test period bronchial lavage was undertaken on the animals under nembutal narcosis. This lavage fluid was processed with the aid of the pneumocystis direct indication test of the company Progen (Progen Biotechnik GmbH, Heidelberg). In this test fluorescein isothiocyanate-marked monoclonal antibodies react with pneumocystis carinii in various development stages, and thus become visible in the fluorescence microscope. In accordance with an evaluation scale which extends in six graduations from 0 to 100, the degree of infection of the respective lavage fluid was determined microscopically.

The result of Compound 1 (Embodiment 1, formula A) is shown in comparison to the known pentamidine isethionate.

TABLE 1

Evaluation of Test for Effectiveness against *Pneumocystis carinii*.

| No. of substs. tested | No. of Animals | Microscopic Evaluation |
|---|---|---|
| 1 | 9 | ++, ++, +, +, +−, +−, + −, +−, (+) |
| 2 | 11 | −, (+), ++, +, ++, +, (+), +−, +, ++, +− |
| 3 | 10 | +, ++, +−, +−, +, +−, ++, +++, +++, ++ |
| 4 | 11 | ++, +++, ++, ++, +++, ++, +++, +++, +++, +++ |
| 5 | 11 | ++, +++, ++, ++, +, ++, +, +, ++, +,+ |
| 6 | 19 | ++, ++, +++, ++, ++, ++, +−, +, ++, ++, ++, +, ++, ++, ++, +++, +++, +, +++ |
| 7 | 10 | −, (+), −, −, −, −, (+), −, −, − |

1 = diacetyl-4,4'-Pentamethylendioxidebenzamidoxim; 23 mg/kg - oral (pre-dissolved in 5% DMSO and filled with 0.04 Tylose; Formula A, Embodiment 1).
2 = pentamidine isethionate in distilled water; 20 mg/kg- i.m.
3 = pentamidine isethionate in distilled water; 40 mg/kg- i.m.
4 = pentamidine isethionate in distilled water; 20 mg/kg - oral
5 = pentamidine isethionate in distilled water; 40 mg/kg - oral
6 = untreated animals, immunosuppressed by dexamathason premedication
7 = untreated animals, not immunosuppressed

| Evaluation Table: | | |
|---|---|---|
| +++ | = | 100 infection |
| ++ | = | 75 |
| + | = | 50 |
| +− | = | 25 |
| (+) | = | 10 |
| − | = | 0 |

| No. tested substances | No. of Animals | Median value | Standard dev. | Reduction (in %) |
|---|---|---|---|---|
| 1 | 9 | 40 | 24 | 44.6 |
| 2 | 11 | 45 | 25 | 37.7 |
| 3 | 10 | 60 | 29 | 16.9 |
| 4 | 11 | 82 | 30 | — |
| 5 | 11 | 66 | 17 | 8.7 |
| 6 | 19 | 72 | 19 | — |
| 7 | 10 | 2 | 4 | — |

As is to be seen from Table 1, compound 1 reveals substantially greater effectiveness against pneumocystis carinii than the known pentamidine isethionate. It is particularly noteworthy that compound 1 when applied orally showed high effectiveness, whereas the known pentamidine isethionate only had any therapeutic effect when applied parenterally.

In order to illustrate the effectiveness of the compound 1 own above (Embodiment 1, Formula A) against trypanosome infections, the test shown below was carried out. In this case effectiveness against the following was investigated:

the animal-pathogenic exciters trypanosoma brucei, trypanosoma vivax, trypanosoma congolense and trypanosoma evansi, as well as the exciter of human sleeping sickness, trypanosoma rhodesiense.

Tests were carried out on a mouse model, the known pentamidine isethionate serving as a comparative substance. The substance to be tested was administered subcutaneously to the animals infected with the respective trypanosoma lines. As a control, the same number of infected animals was left untreated. After observation for 3 weeks, the number of cured animals, the dosis curativa (D. A.), the relapse dose (R. D.) and the inhibitor dose (H. D.) were determined. The results of these tests are given by way of example in tables 2 to 6; further detailed data on the test methods used are also to be found in these tables.

TABLE 2

Effect of Diacetyl-4,4'-Pentamethylendioxydibenzami-doxim (1) against *Trypanosoma brucei* (line 8/18) in the NMRI mouse

| Test Animal: | Albino mouse (HOE; NMRKF; SPF 71), KGW 17–18 g |
| --- | --- |
| Inoculation: | 1 × 10$^5$ Trypanosomes from N$_2$ Stability per mouse, intraperitoneally |
| Treatment: | 2 × subcutaneous (1 h before, 1 h after infection) |
| Test Duration: | 21 days |

| Preparation (solubility) | Dose mg/kg base | Survival times days after infection | | | | | No. of animals cured/in all | Effect |
| --- | --- | --- | --- | --- | --- | --- | --- | --- |
| 1 | 30 | 21 | 21 | 21 | 21 | 21 | 5/5 | DC |
| (DMSO-MEIS- | 10 | 21 | 21 | 21 | 21 | 21 | 5/5 | DC |
| embryo oil) | 3 | 21 | 21 | 21 | 21 | 21 | 5/5 | DC |
|  | 1 | 10 | 12 | 20 | 21 | 21 | 2/5 | RD |
| Pentamidin-17 | (10) | 21 | 21 | 21 | 21 | 21 | 5/5 | DC |
| Isethionat 5.2 | (3) | 21 | 21 | 21 | 21 | 21 | 5/5 | DC |
| (a. dist.) 1.7 | (1) | 21 | 21 | 21 | 21 | 21 | 5/5 | DC |
| infected untreated controls (IK) | 0 | 5 | 5 | 5 | 5 | 5 | 0/5 | — |

DC = dosis curativa
RD = relapse dose

TABLE 3

Effect of Diacetyl-4,4¹-Pentamethylendioxydibenzamidoxim (1) against *Trypanosoma vivax* (line Zaria Y58) in the NMRI mouse.

| Test Animal: | Albino mouse (HOE; NMRKF; SPF 71), KGW 18–20 g |
| --- | --- |
| Inoculation: | 1 × 10$^4$ Trypanosoma from N$_2$ stabilisate per mouse intraperitoneally |
| Treatment: | 1 × subcutaneous (2 days after infection) |
| Test duration: | 25 days |

| Preparation (solubility) | Dose mg/kg base | Survival times days after infection | | | | | No. of animals cured/in all | Effect |
| --- | --- | --- | --- | --- | --- | --- | --- | --- |
| 1 | 30 | 21 | 21 | 21 | 21 | 21 | 0/5 | DC |
| (DMSO-Meis-10 |  | 15 | 17 | 17 | 21 | 21 | 0/5 | HD |
| embryo oil | 3 | 10 | 10 | 14 | 21 | 21 | 0/5 | ineffective |
| Pentamidine-52 | (30) | 21 | 21 | 21 | 21 | 21 | 5/5 | DC |
| isethionat 17 | (10) | 21 | 21 | 21 | 21 | 21 | 5/5 | DC |
| (A.dist.) 5,2 | (3) | 20 | 21 | 21 | 21 | 21 | 3/5 | RD |
| 1.7 | (1) | 15 | 21 | 21 | 21 | 21 | 0/5 | HD |
| Infected untreated Controls (IK) | 0 | 9 | 13 | 15 | 21 | 21 | 0/5 | — |

DC = Dosis curativa
RD = Relapse dose
HD = inhibiting dose.

TABLE 4

Effect of Diacetyl-4,4'-Pentamethylenedioxydibenzamidoxim (1) against *Trypanosoma evansi* (line Bogor) in the NMRI mouse.

| Test Animal: | Albino mouse (HOE; NMRKF; SPF 71), KGW 18–20 g |
| --- | --- |
| Inoculation: | 1 × 10$^4$ Trypansomes from N$_2$ stabilisate per mouse intraperitoneally |
| Treatment: | 1 × subcutaneous (2 days after infection) |
| Test duration: | 21 days |

| Preparation (solubility) | Dose mg/kg base | Survival times days after infection | | | | | No. of animals cured/in all | Effect |
| --- | --- | --- | --- | --- | --- | --- | --- | --- |
| 1 | 30 | 3 | 3 | 3 | 3 | 4 | 0/5 | HD |
| (Dmso Meis | 10 | 3 | 4 | 4 | 4 | 4 | 0/5 | HD |
| embryo oil | 3 | 3 | 3 | 3 | 4 | 5 | 0/5 | HD |
| Pentamidine-52 | (30) | 6 | 8 | 8 | 9 | 21 | 1/5 | RD |
| Isethionate 17 | (10) | 5 | 5 | 5 | 5 | 5 | 0/5 | HD |
| (A. dist.) Infected untreated Controls (IK) | 0 | 2 | 2 | 2 | 3 | 4 | 0/5 | — |

DC = Dosis curativa
RD = relapse dose
HD = inhibiting dose

TABLE 5

Effect of Diacetyl-4,4'-Pentamethylenedioxydibenzamidoxim (1) against *Trypanosona rhodesiense* '3176' (berenil-resistant) in the NMRI mouse.

| Test Animal: | Albino mouse (HOE; NMRKF; SPF 71), KGW 17–20 g |
| --- | --- |
| Inoculation: | 1 × 10$^3$ Trypanosomes from N$_2$ stabilisate per mouse intraperitoneally |
| Treatment: | 1 × subcutaneous (1 day after infection) |
| Test duration: | 21 days |

| Preparation (solubility) | Dose mg/kg base | Survival times days after infection | | | | | No. of animals cured/in all | Effect |
| --- | --- | --- | --- | --- | --- | --- | --- | --- |
| 1 | 30 | 21 | 21 | 21 | 21 | 21 | 5/5 | DC |
| (DMSO-Meis | 10 | 18 | 18 | 20 | 21 | 21 | 1/5 | RD |
| embryo oil | 3 | 5 | 14 | 14 | 14 | 21 | 1/5 | RD |
| Pentamidine 52 | (30) | 21 | 21 | 21 | 21 | 21 | 5/5 | DC |
| Isethionat 17 | (10) | 21 | 21 | 21 | 21 | 21 | 5/5 | DC |
| (A.dist.)5,2 | (3) | 20 | 21 | 21 | 21 | 21 | 4/5 | RD |
| 1.7 | (1) | 10 | 16 | 21 | 21 | 21 | 3/5 | RD |
| infected untreated controls (IK) | 0 | 3 | 3 | 3 | 4 | 4 | 0/5 | — |

DC = Dosis curativa
RD = Relapse dose
HD = inhibiting dose

TABLE 6

Effect of Diacetyl-4,4'-pentamethylenedioxydibenzamidoxim (1) against *Trypanosoma congolense* (Liverpool) in the NMRI mouse.

| Test Animal: | Albino mouse (HOE; NMRKF; SPF 71), KGW 18–20 g |
| --- | --- |
| Inoculation: | 1 × 10$^4$ Trypansomes from N$_2$ stabilisate per mouse intraperitoneally |
| Treatment: | 1 × subcutaneous (3 days after infection) |
| Test duration: | 21 days |

| Preparation (solubility) | Dose mg/kg base | Survival times days after infection | | | | | No. of animals cured/in all | Effect |
| --- | --- | --- | --- | --- | --- | --- | --- | --- |
| 1 | 30 | 9 | 9 | 9 | 10 | 21 | 0/5 | ineffective |
| DMSO Meis- | 10 | 21 | 21 | 21 | 21 | 21 | 0/5 | ineffective |
| embryo oil) | 3 | 9 | 21 | 21 | 21 | 21 | 0/5 | ineffective |

TABLE 6-continued

Effect of Diacetyl-4,4'-pentamethylenedioxydibenzamidoxim (1) against *Trypanosoma congolense* (Liverpool) in the NMRI mouse.

|  | 1 |  |  |  |  |  |  |  |
|---|---|---|---|---|---|---|---|---|
| Pentamidine52 | (30) | 21 | 21 | 21 | 21 | 21 | 0/5 | ineffective |
| Isethionate17 | (10) | 21 | 21 | 21 | 21 | 21 | 4/5 | RD |
| (A. dist.)5.2 | (3) | 12 | 21 | 21 | 21 | 21 | 0/5 | RD |
| Infected untreated Controls (IK) | 0 | 10 | 10 | 13 | 21 | 21 | 0/5 | ineffective |
|  |  | 13 | 21 | 21 | 21 | 21 | 0/5 | — |

DC = *Dosis curativa*
RD = Relapse dose
HD = inhibiting dose.

As is to be seen from Tables 2 and 6, compound 1 reveals good effectivity against the exciter Trypanosoma which, due to its relationship to the human-pathogenic trypanosomes, as an animal-pathogenic exciter, serves as a model for study of human sleeping sickness. Compound 1 is also effective against infection with the human-pathogenic exciter Trypanosoma rhodesiense.

In comparison to the known pentamidine isethionate, however, a slightly weaker effectivity of compound 1 was observed against Trypanosoma brucei and Trypanosoma rhodesiense. Compound 1 was only slightly less effective against Trypanosoma vivax and Trypanosoma evansi. The compound 1 was ineffective against infections with Trypanosoma congolense.

The test results show that the range of effectivity revealed by the new pharmaceutical preparation is identical with that of pentamidine diisethionate. It reveals itself as slightly less effective with some trypanosome species. Despite this, the new preparation represented a clear improvement over existing possible therapies as, in contrast to pentamidine diisethionate, this medicine need not be administered parenterally. Due to the elimination of the side-effects involved in the form of administration, the novel pharmaceutical preparation has the advantage that for the first time, even in areas with poor medical provision, blanket therapy and prophylaxis against trypanosome infections can be carried out. In addition, it is possible to treat patients who manifest a central-nervous trypanosome infection, without having to accept the serious, sometimes lethal side-effects of the previously-used therapeutic agents containing arsenic.

In order to illustrate the pharmaceutical effectivity against Leishmanioses, the following test was carried out.

The test was undertaken on hamsters, which were infected with Leishmania donovani. The substances to be tested in each case were administered subcutaneously at various dosages, and their effectivity compared to that of the known pentamidine isethionate. Infected, untreated animals were used as control groups.

After 8 days the number of Leishmania per liver-cell nucleus, and liver weight, were determined in accordance with the model of Stauber et al. J. Protozool. 5, 269–273 (1958).

Table 7 shows more detail of the test using the example of compound 1 (formula A, Embodiment 1).

TABLE 7

Effect of Diacetyl-4,4'-Pentamethylenedioxydibenzamidoxim (1) against *Leishmania donovani* in the hamster (Stauber model)

| Test animal: | Syrian gold hamster (Ivanovas, Kiss legg, Allgäu) KGW 70–80 g |
| Inoculation: | 1 × 10⁷ Leishmania (animal intravenous (upper brachial vein) |
| Treatment: | 5 × subcutaneous (3 h, 1, 2, 3 und 4 days after infection) |
| Test duration: | 8 days (killing and dissection of animals) |

| Preparation (solubility) | Dose mg/kg (base) | No. of animals | No. Leishmania/Cell nucl. × Liver weight (mg) indiv. values per animal × | | | | | | Effect (s) |
|---|---|---|---|---|---|---|---|---|---|
| 1 (DMSO-8 Tween 80 (Aqua. dist.) | 25 12,5 | 5 5 | 0 0 | 0 0 | 0 0 | 196 276 | 412 335 | 122 122 | (183) (168) |
| Pentamidin-43 Isethionate21.5 (Aqua dist.) | (25) (12,5) | 5 5 | 0 0 | 0 0 | 0 0 | 0 0 | 0 0 | 0 0 | |
| Infected untreated controls (IK) | 0 | 5 | 1217 | 1697 | 2214 | 2303 | 2884 | 2063 | (633) |

DC = *Dosis curativa*
RD = Relapse dose
HD - inhibiting dose.

As is to be seen from Table 7, compound 1 (Embodiment 1, Formula A) shows clear-cut effectivity against Leishmania donovani.

I claim:

1. A pharmaceutical preparation for oral administration comprising a conventional carrier and an active ingredient having the general formula I.

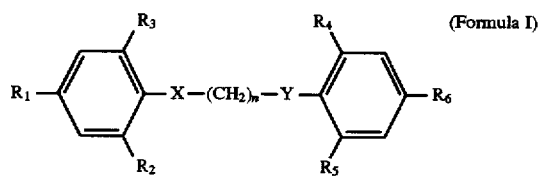

(Formula I)

wherein, $R_1$ and $R_6$ are identical or different, and are selected from the group consisting of:

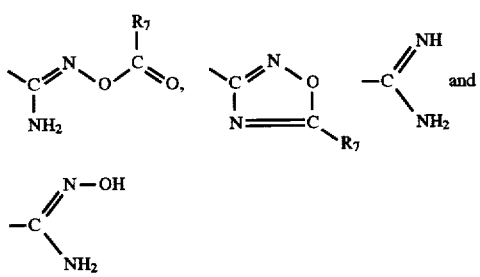

R$_7$ is selected from the group consisting of hydrogen, an alkyl residue and an aryl residue, R$_2$, R$_3$, R$_4$, and R$_5$ are identical or different and are selected from the group consisting of hydrogen, —NO$_2$, halogen and an OR$_8$ grouping;

R$_8$ is selected from the group consisting of hydrogen and an alkyl group;

X and Y are identical or different, and are selected from the group consisting of oxygen, nitrogen and sulphur; and n is a whole number between 0 and 8;

and their salts, with the proviso that when X and Y are both oxygen, R$_2$, R$_3$, R$_4$, and R$_5$ are each hydrogen, n is 5 and R$_1$ is

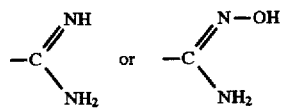

then R$_6$ is selected from the group consisting of

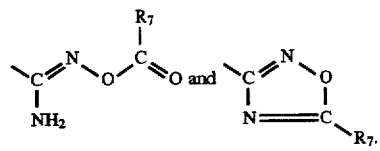

2. A pharmaceutical preparation according to claim 1 wherein R$_1$ and R$_6$ are identical or different, and are selected from the group consisting of

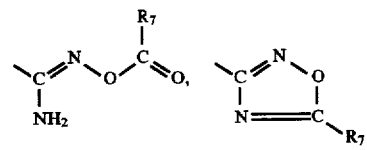

and

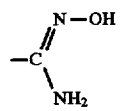

R$_7$ is hydrogen, an alkyl residue or an aryl residue, and their salts.

3. A pharmaceutical preparation according to claim 1 or 2 wherein R$_7$ is a C$_{12}$–C$_{18}$ alkyl residue.

4. A pharmaceutical preparation according to claim 1 or 2 wherein R$_7$ is a C$_1$–C$_4$ alkyl group.

5. A pharmaceutical preparation according to claim 1 or 2 wherein R$_1$ and R$_6$ are identical.

6. A pharmaceutical preparation according to claim 1 or 2 wherein n is a whole number between 2 and 6.

7. A pharmaceutical preparation according to claim 1 or 2 wherein at least one of R$_2$, R$_3$, R$_4$, and R$_5$ is OCH$_3$.

8. A pharmaceutical preparation according to claim 1 or 2 wherein the preparation contains the active ingredient in a concentration between 0.1% by weight and 50% by weight.

9. A pharmaceutical preparation according to claim 1 or 2 wherein the preparation contains a mixture of active ingredients of the general formula I.

10. A pharmaceutical preparation according to claim 1 or 2 wherein the preparation contains at least one active ingredient of the following formulae II to IV shown hereafter, or a salt of these active ingredients:

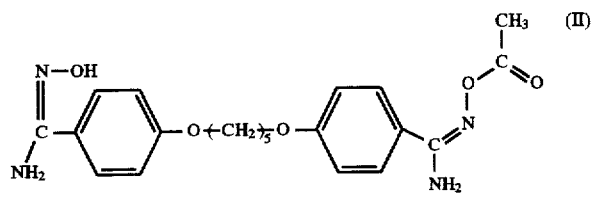

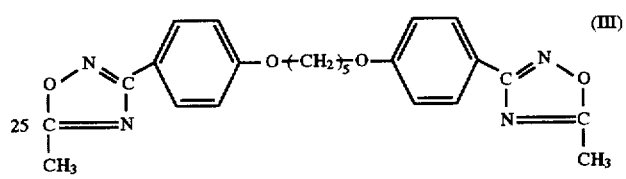

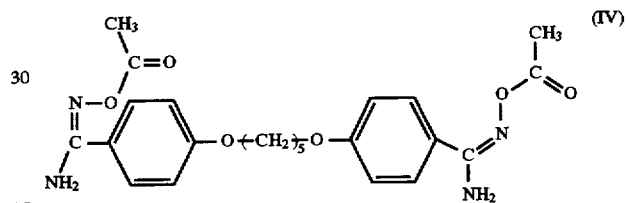

11. The pharmaceutical preparation according to claim 1 or 2 for producing a medicament for prophylaxis and/or therapy of pneumocystis carinii pneumonia, particularly also in severe cases with extrapulmonary manifestation.

12. The pharmaceutical preparation according to claim 1 or 2 for producing a medicament for prophylaxis and/or therapy of animal or human trypanosome infections, particularly also in cases with central-nervous manifestation.

13. The pharmaceutical preparation according to claim 1 or 2 for producing a medicament for prophylaxis and/or therapy of Leishmanioses.

14. A pharmaceutical preparation according to claim 4 wherein R$_7$ is CH$_3$.

15. A medicament for prophylaxis and/or therapy of pneumocystis carinii pneumonia comprising a pharmaceutical preparation according to claim 1.

16. A medicament for prophylaxis and/or therapy of animal or human trypanosome infections comprising a pharmaceutical preparation according to claim 1.

17. A medicament for prophylaxis and/or therapy of Leishmanioses comprising a pharmaceutical preparation according to claim 1.

18. A compound having the general formula I,

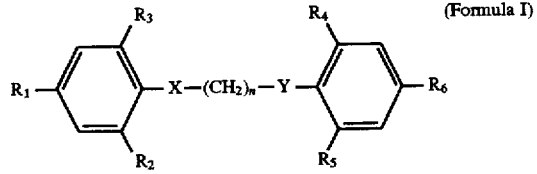

wherein $R_1$ and $R_6$ are identical or different, and are selected from the group consisting of:

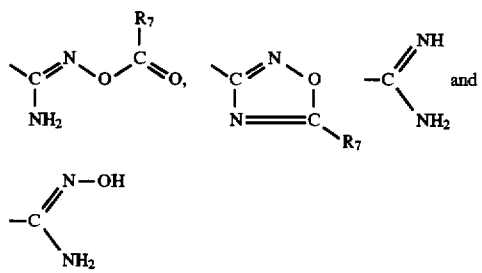

$R_7$ is selected from the group consisting of hydrogen, an alkyl residue and an aryl residue, $R_2$, $R_3$, $R_4$, and $R_5$ are identical or different and are selected from the group consisting of hydrogen, —$NO_2$, halogen and an $OR_8$ grouping;

$R_8$ is selected from the group consisting of hydrogen and an alkyl group;

X and Y are identical or different, and are selected from the group consisting of oxygen, nitrogen and sulphur; and n is a whole number between 0 and 8;

and their salts, with the proviso that when X and Y are both oxygen, $R_2$, $R_3$, $R_4$, and $R_5$, are each hydrogen, n is 5 and $R_1$ is

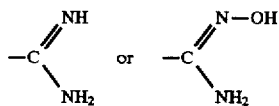

then $R_6$ is selected from the group consisting of

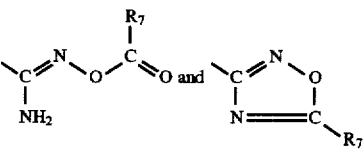

19. A compound according to claim 18 wherein $R_1$ and $R_6$ are identical or different, and are selected from the group consisting of

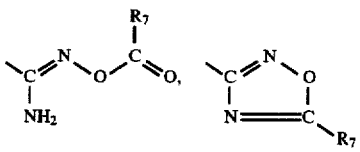

and

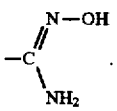

20. A compound according to claim 18 wherein $R_1$ and $R_6$ are identical.

21. A compound according to claim 18 wherein n is a whole number between 2 and 6.

22. A compound according to claim 18 wherein at least one of $R_2$, $R_3$, $R_4$, and $R_5$ is $OCH_3$.

23. A compound according to claim 18 wherein $R_7$ is a $C_1$-$C_4$ alkyl group.

24. A compound according to claim 23 wherein $R_7$ is $CH_3$.

* * * * *